United States Patent
Moruzzi

(10) Patent No.: US 6,610,990 B1
(45) Date of Patent: Aug. 26, 2003

(54) UV LIGHT SOURCE

(75) Inventor: James Lodovico Moruzzi, Berkshire (GB)

(73) Assignee: Quay Technologies Ltd., Berks (GB)

( * ) Notice: Subject to any disclaimer, the term of this patent is extended or adjusted under 35 U.S.C. 154(b) by 0 days.

(21) Appl. No.: 10/048,286

(22) PCT Filed: Jul. 26, 2000

(86) PCT No.: PCT/EP00/07288

§ 371 (c)(1),
(2), (4) Date: Jan. 29, 2002

(87) PCT Pub. No.: WO01/09924

PCT Pub. Date: Feb. 8, 2001

(30) Foreign Application Priority Data

Jul. 29, 1999 (GB) ............................................... 9917661
May 9, 2000 (GB) ............................................... 0011039

(51) Int. Cl.[7] ................................................. A61N 5/06
(52) U.S. Cl. ................. 250/504 R; 210/209; 210/198.1
(58) Field of Search ........................... 313/570; 422/24; 250/504 R; 210/209, 198.1

(56) References Cited

U.S. PATENT DOCUMENTS

| 3,911,318 A | 10/1975 | Urv et al. |
| 5,166,528 A | 11/1992 | Le |
| 5,614,151 A * | 3/1997 | LeVay et al. .................. 422/24 |
| 5,686,793 A * | 11/1997 | Turner et al. ................ 313/570 |
| 6,200,466 B1 * | 3/2001 | Bender ....................... 210/96.1 |

FOREIGN PATENT DOCUMENTS

| JP | 61 046290 A | 3/1986 |
| JP | 05 243138 A | 12/1993 |
| WO | 96 09842 A | 4/1996 |
| WO | 96 40298 A | 12/1996 |
| WO | WO 00/32244 | 6/2000 |

* cited by examiner

Primary Examiner—John R. Lee
Assistant Examiner—Phillip A Johnston
(74) Attorney, Agent, or Firm—Birch, Stewart, Kolasch & Birch, LLP

(57) ABSTRACT

There is described an ultraviolet light source comprising an ultraviolet lamp, a microwave energy source for exciting said ultraviolet lamp and an enclosure for enclosing the ultraviolet lamp, the enclosure comprising an optically transparent waveguide. The ultraviolet light source is particularly suitable for use in the promotion of photochemical reactions and of molecular dissociation in liquids.

43 Claims, 9 Drawing Sheets

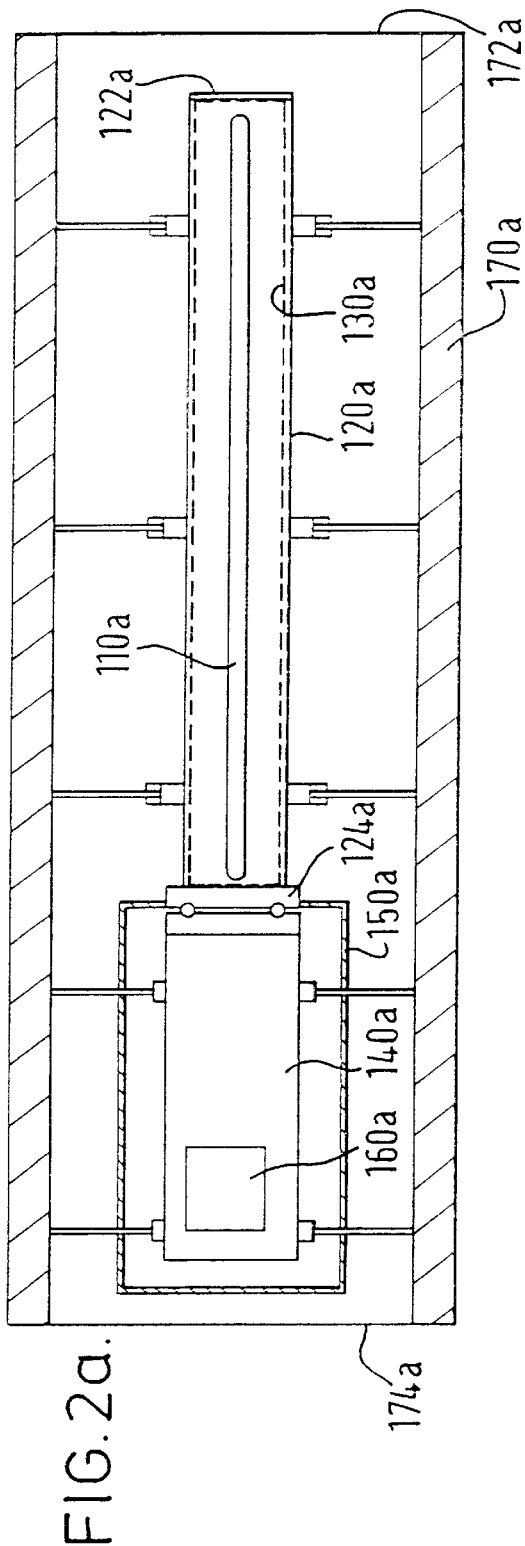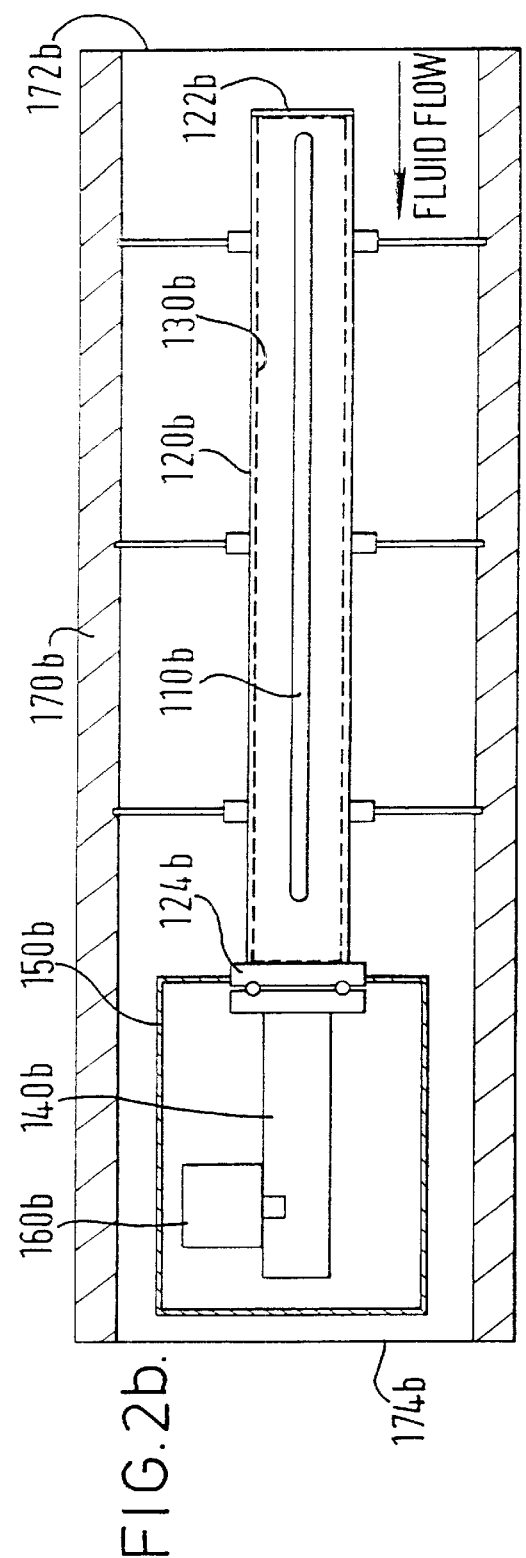

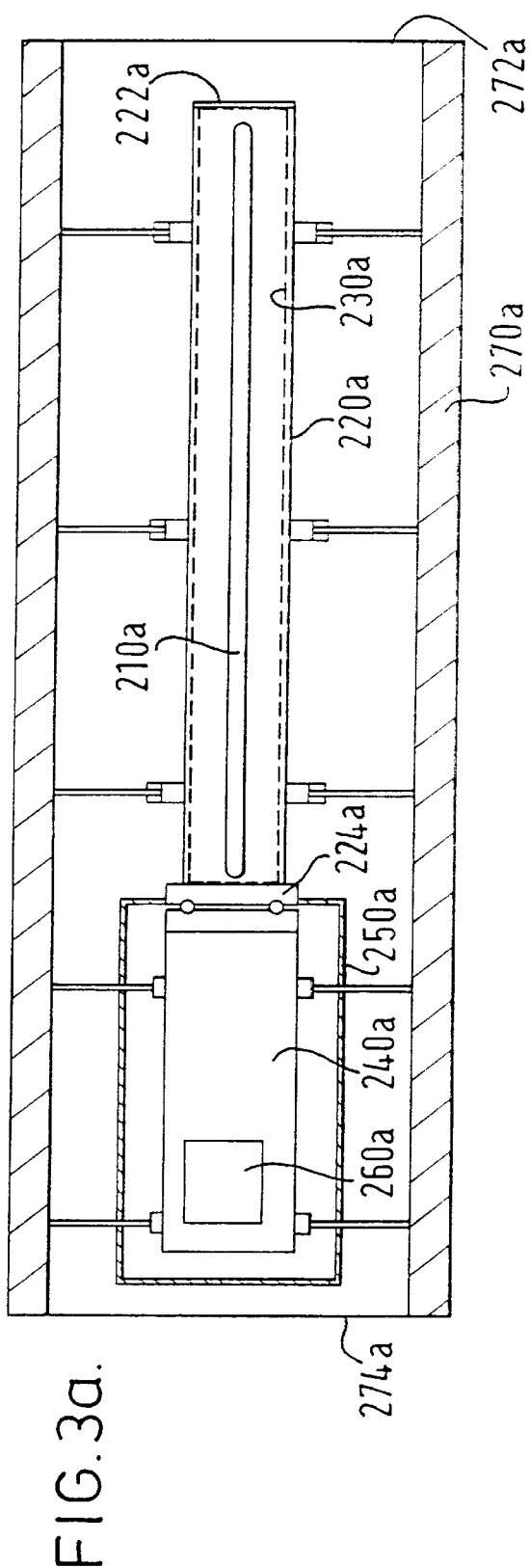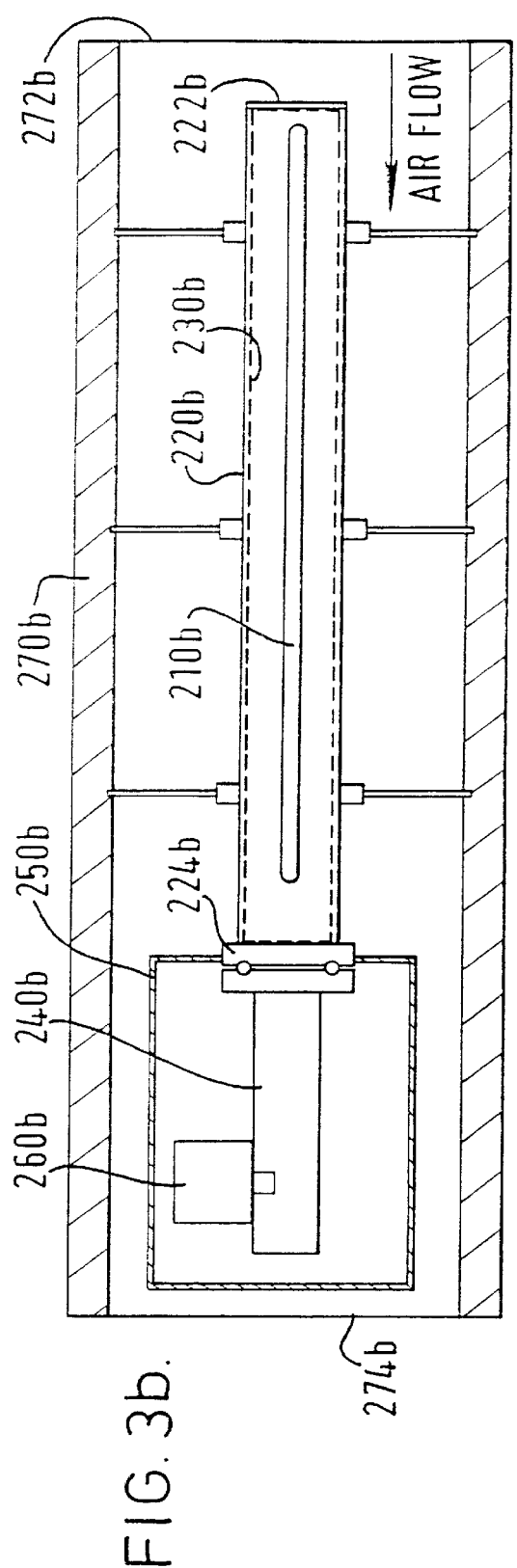
FIG. 3a.
FIG. 3b.

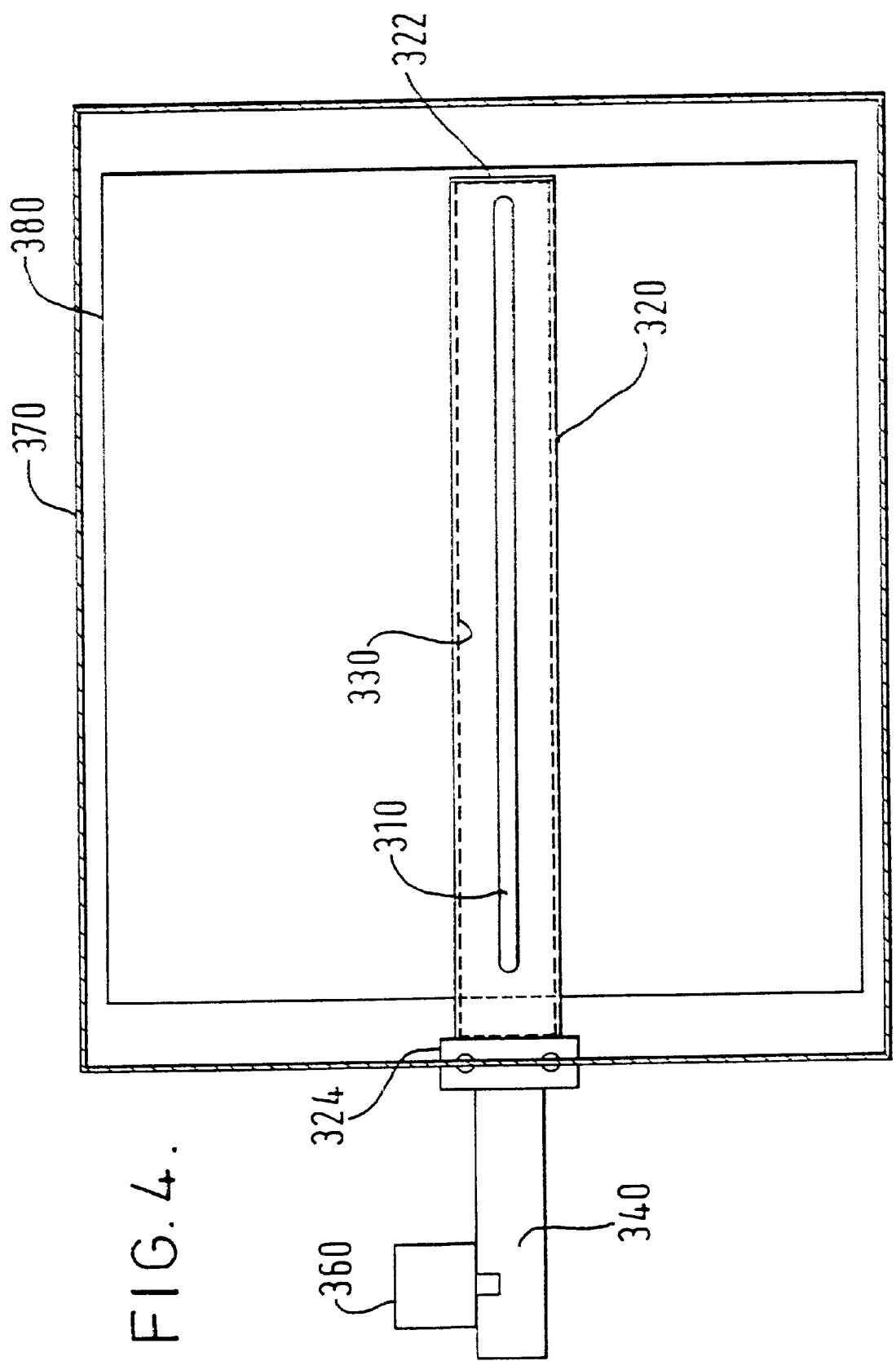

UV LIGHT SOURCE

This application is the national phase under 35 U.S.C. §371 of PCT International Application No. PCT/EP00/07288 which has an International filing date of Jul. 26, 2000, which designated the United States of America and was published in English.

TECHNICAL FIELD

The present invention is in the field of ultraviolet (UV) light sources.

BACKGROUND OF THE INVENTION

It is known to use ultraviolet (UV) radiation for a variety of uses including those involving the promotion of photochemical reactions and of molecular dissociation.

One problem with known systems is that it is difficult to safely provide sufficient excitation energy to the UV source and difficult to effectively transfer that energy to the substance or entity to be treated. It is therefore difficult to arrange systems for high energy, high throughput industrial purposes.

There is now described an ultraviolet light source which enables efficient, high throughput UV treatment to be conducted. The ultraviolet light source comprises an UV lamp which is excited by a microwave energy source. The lamp is enclosed by a waveguide comprising UV transparent material. The ultraviolet light source is particularly suitable for the treatment of liquids which are flowed past the ultraviolet light source.

SUMMARY OF THE INVENTION

According to one aspect of the present invention there is provided an ultraviolet light source comprising an ultraviolet bulb; a microwave energy source for exciting said ultraviolet bulb; and an enclosure for enclosing the ultraviolet bulb, the enclosure comprising an optically transparent waveguide.

The dominant wavelength of the ultraviolet light source is either (a) from 140 to 240 nm, preferably from 150 to 220 nm, most preferably from 160 to 200 nm, particularly 182 nm or 185 nm and the ultraviolet light source is suitable for use in promoting molecular dissociation reactions; or (b) from 300 to 400 nm, preferably from 320 to 380 nm, most preferably from 330 to 370 nm, particularly 346 nm and the ultraviolet light source is suitable for use in promoting photochemical reactions.

By optically transparent waveguide it is meant a waveguide that is substantially transparent to the ultraviolet radiation employed herein, typically having a transparency of greater than 50%, preferably greater than 90% to UV radiation.

The waveguide controls the flow of ultraviolet radiation from the enclosure. The control function typically includes the prevention of the release of harmful or unnecessary ultraviolet radiation frequencies. The exact nature of the waveguide and its control function can be tailored to fit the purpose of use.

Suitably, the ultraviolet bulb has no electrode. That is to say it is an electrode-less bulb such as one comprising a partially evacuated tube comprising an element or mixtures of elements in vapour form. Mercury is a preferred element for this purpose, but alternatives include mixtures of inert gases with mercury compounds, sodium and sulphur. Halides, such as mercury halide are also suitable herein. Amalgams are also suitable herein including indium/mercury amalgam.

In one aspect, the waveguide controls the flow of microwave energy from the enclosure. Control of the microwave energy which passes through the waveguide is useful in embodiments of the invention which make use of both UV and microwave radiation.

In another aspect, the waveguide blocks at least the majority of the flow of microwave energy from the enclosure.

Suitably, the enclosure comprises quartz or a UV-transparent plastic material.

Suitably, the enclosure is coated with a coating which assists in controlling the flow of ultraviolet and/or microwave energy therefrom. The coating may be applied to either or both of the inner or outer surfaces of the enclosure. Partial coatings are also envisaged.

Suitably, a system for cleaning the enclosure (e.g. the quartz tube) is incorporated herein. Suitable cleaning systems include those based upon fluid flow, such as flow of water, air or gas. Cleaning agents such as detergents may be employed as necessary.

Suitably, the waveguide comprises a conducting material. The conducting material may be integral, or applied as an internal or external coating or liner. The liner may directly contact the inner surface of the enclosure or be spaced therefrom.

Suitably, the waveguide comprises a conducting mesh. Preferably, the conducting mesh comprises a high frequency conducting material selected from the group consisting of copper, aluminium and stainless steel.

The ultraviolet bulb has any suitable shape and size, including elongate forms such as a cigar-shape. The bulb size can be tailored. Typical bulb diameters are from 5 to 200 mm, for example 38 mm.

Embodiments are envisaged in which plural bulbs are employed. The bulb may be similar in type e.g. of similar size and operating temperature or combinations of different bulb types may be employed. The number of bulbs employed is tailored to the purpose of use. Typically from 2 to 25 bulbs are employed, such as from 3 to 18 bulbs. Various forms of arrangement of the plural bulbs are envisaged including random or informal arrangements, side-by-side arrangements, sequential arrangements, array arrangements and clusters. The bulbs may be arranged in serial, parallel or mixed serial and parallel electrical circuit arrangements.

The optically transparent waveguide has any suitable shape, such as cylindrical or rectangular forms. The length and size of the waveguide is tailored to fit the particular purpose of use and to accommodate the necessary bulb(s).

Suitably, the ultraviolet bulb has an operating temperature which maximises the chosen bulb characteristics. Typical operating temperatures are from 10° C. to 900° C., and the operating temperature will be selected and optimised according to the purpose of use.

Suitably, the microwave energy source comprises a magnetron. Alternative sources are envisaged such as solid state devices.

Suitably, the ultraviolet light source additionally comprises a system for cleaning the enclosure.

Suitably, the ultraviolet light source additionally comprises a pathguide to guide the microwave energy from the microwave energy source to the ultraviolet bulb.

In one aspect the pathguide defines an essentially linear path for the microwave energy.

In another aspect, the pathguide defines a non-linear path such as a path defining an angle, such as a right angle.

Suitably, the pathguide comprises a coaxial cable.

Suitably, the ultraviolet light source additionally comprises a housing for said enclosure. Preferably, the housing has an inlet and an outlet and the housing is shaped to guide fluid flow from the inlet, past the enclosure to the outlet. Preferably, the fluid comprises air or a liquid such as water. Suitably, the ultraviolet light source additionally comprises a pump for pumping fluid from the inlet, past the enclosure to the outlet. Alternatively, gravity may be utilised to encourage fluid flow.

The choice of materials for use in the housing and any fluid flow piping arrangements can be important. Typically, the materials will be selected which are resistant to corrosion and which do not leach contaminants to the system.

Seal materials are also carefully selected with typical seal materials including Chemraz (trade name), Teflon (trade name), encapsulated Viton (trade name) and GORE-TEX (trade name).

According to another aspect of the present invention there is provided a lamp comprising an ultraviolet bulb, said bulb being excitable by microwave energy; and an enclosure for enclosing the ultraviolet bulb, the enclosure comprising an optically transparent waveguide.

The dominant wavelength of the lamp is either
(a) from 140 to 240 nm, preferably from 150 to 220 nm, most preferably from 160 to 200 nm, particularly 182 nm or 185 nm and the lamp is suitable for use in promoting molecular dissociation reactions; or
(b) from 300 to 400 nm, preferably from 320 to 380 nm, most preferably from 330 to 370 nm, particularly 346 nm and the lamp is suitable for use in promoting photochemical reactions.

Preferably, the ultraviolet bulb has no electrode.

According to a further aspect of the present invention there is provided a method of promoting the dissociation of a molecular entity comprising
applying microwave energy to an ultraviolet lamp to produce ultraviolet radiation of dominant wavelength of from 140 to 240 nm; and
exposing the molecular entity to said ultraviolet radiation, wherein
an enclosure encloses the ultraviolet lamp, the enclosure comprising an UV transparent waveguide.

In one aspect, the molecular entity is borne in a fluid such as air or a liquid and the fluid flows past the enclosure. A specific example of this is in the clean up of ballast seawater from the holds of ships wherein contaminants in the ballast water are dissociated by application of ultraviolet radiation.

A further specific example of molecular dissociation applications based on fluid flow is in the dissociation of organic material, such as Total Oxidisable Carbon (TOC) in rinse water for use in the electronics, semiconductors pharmaceuticals, beverage, cosmetics and power industries. The process involves the production of OH.radicals which oxidise any hydrocarbon molecules in the rinse water. Optionally, other oxidants may be employed such as ozone and hydrogen peroxide. Typically, polishing deionisation beds, featuring nuclear-grade resin materials are placed downstream of the TOC reduction units to remove any ionised species and restore the resitivity of the water.

In another aspect, the molecular entity is borne on a surface and the ultraviolet radiation is applied to the surface. The molecular entity may, for example be a contaminant on the surface which is rendered harmless by its molecular dissociation.

In one example, the surface is of a food product such as a meat, dairy, fish, fruit or vegetable product and the ultraviolet radiation is applied to the surface to dissociate any contaminants such as chemical residues including pesticides.

In another example, the surface is an industrially-produced product such as a packaging product for example, a medical packaging product, a foil bag, cup or lid, or a glass or plastic bottle, and the ultraviolet radiation is applied to the surface to dissociate any contaminants arising from the industrial process.

In a further example, the surface is the surface of any equipment used in the manufacture of food products or industrially produced products such as the surface of any reactors or conveyors.

According to a still further aspect of the present invention there is provided a method of promoting a photochemical reaction in a substance comprising
applying microwave energy to an ultraviolet lamp to produce ultraviolet radiation of dominant wavelength of from 300 to 400 nm; and
exposing the entity to said ultraviolet radiation, wherein an enclosure encloses the ultraviolet lamp, the enclosure comprising an UV transparent waveguide.

In one aspect, the substance is borne in a fluid such as air or a liquid and the substance-bearing fluid flows past the enclosure.

In another aspect, the substance is borne on a surface and the ultraviolet radiation is applied to the surface.

Preferably, the substance is selected from the group consisting of surface treatment materials including paints, toners, varnishes (e.g. polyurethane varnishes), stains and laminating materials.

Laminating is for example, used in the production of various electronic components, data storage devices including compact discs and packaging materials including blister packages.

According to a further aspect of the present invention there is provided an ultraviolet light source comprising a plurality of ultraviolet bulbs; a microwave energy source for exciting said plurality of ultraviolet bulbs; and an enclosure for enclosing the plurality of ultraviolet bulbs, the enclosure comprising an optically transparent waveguide.

According to a further aspect of the present invention there is provided a lamp comprising a plurality of ultraviolet bulbs, said plurality of bulbs being excitable by microwave energy; and an enclosure for enclosing the plurality of ultraviolet bulbs, the enclosure comprising an optically transparent waveguide.

BRIEF DESCRIPTION OF THE DRAWINGS

Preferred embodiments of the ultraviolet light source in accord with the present invention will now be described with reference to the accompanying drawings in which:

FIGS. 2a and 2b are schematic representations of second and third ultraviolet light sources herein;

FIGS. 3a and 3b are schematic representations of fourth and fifth ultraviolet light sources herein;

FIG. 4 is a schematic representation of a sixth ultraviolet light source herein suitable for use in combined UV and microwave methods;

DETAILED DESCRIPTION OF THE INVENTION

The present invention is here described by means of examples, which constitute possible embodiments of the invention.

Figure 1:
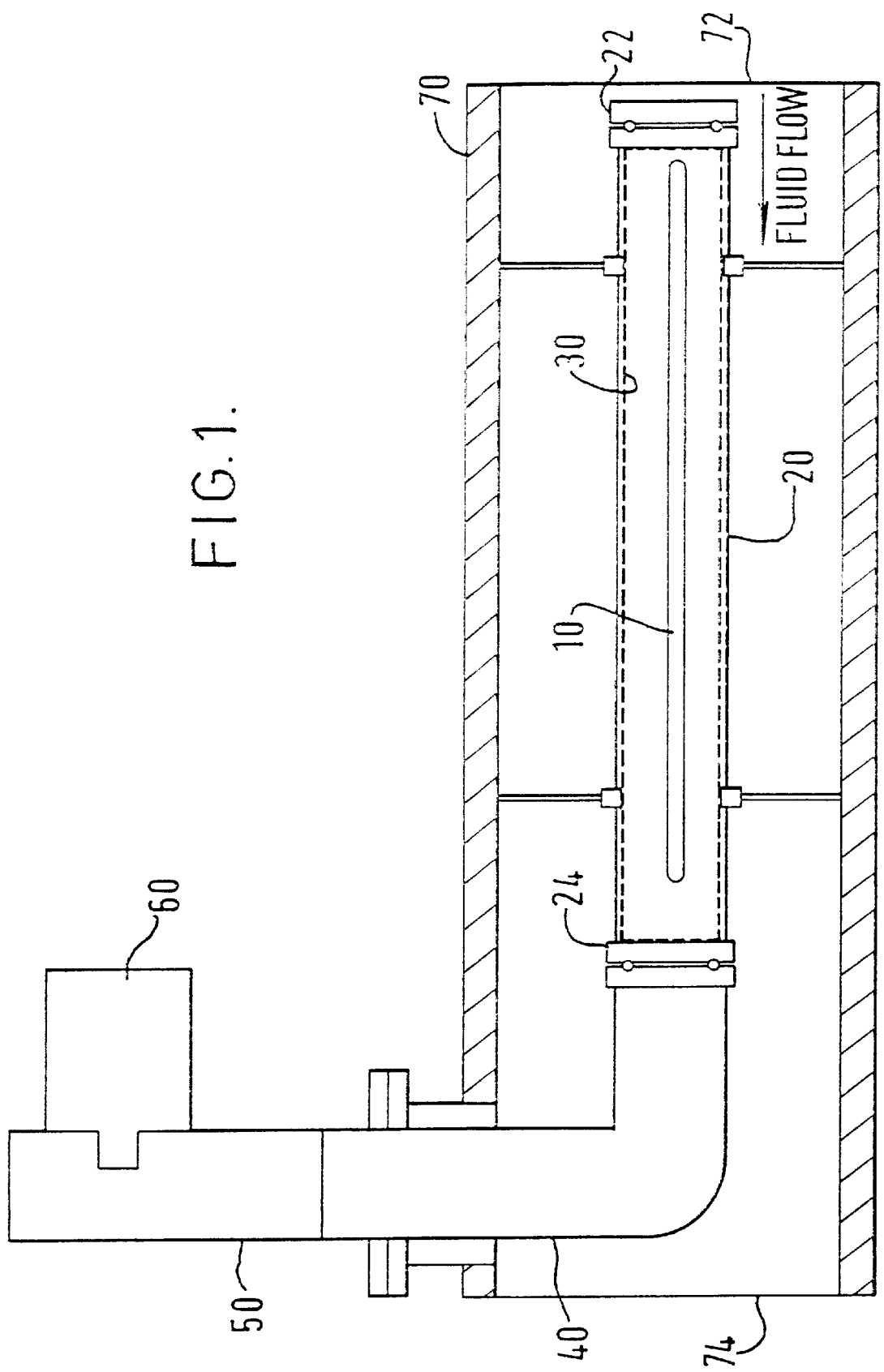
FIG. 1 is a schematic representation of a first ultraviolet light source herein.

FIG. 1 shows an ultraviolet light source comprising an ultraviolet lamp 10 enclosed by cylindrical enclosure 20. The cylindrical walls of the enclosure 20 form a waveguide and are comprised of quartz material which is transparent to UV radiation. A conducting copper mesh 30 is provided to the inner surface of the waveguide. First end of the cylindrical enclosure has blocking end flange 22 provided thereto. The second end is provided with coupling flange 24 which couples with right angled pathguide 40 which in turn connects with rectangular pathguide 50. Magnetron 60 acts as a microwave energy source to feed microwaves into the rectangular waveguide 50, thence into the right angled pathguide 40 and finally to the ultraviolet lamp 10 which is excited thereby.

The enclosure 20 is within tubular housing 70. The housing 70 has a fluid inlet 72 and a fluid outlet 74 provided thereto. In use, fluid flows from the inlet 72 past the enclosure 20 and towards the outlet 74. As the fluid flows past the enclosure 20 it is irradiated with UV radiation produced by the ultraviolet lamp 10. The radiation itself passes through the UV transparent walls of the enclosure 120a, 120b to contact the fluid.

FIGS. 2a and 2b show related ultraviolet light sources herein. Both comprise ultraviolet mercury discharge lamp 110a, 110b enclosed by cylindrical enclosure 120a, 120b. The cylindrical walls of the enclosure 120a, 120b form a waveguide and are comprised of quartz material which is transparent to UV radiation. A conducting copper mesh 130a, 130b is provided to the inner surface of the waveguide. The enclosure 120a, 120b has air or nitrogen circulating therein. First end of the cylindrical enclosure has blocking end flange 122a, 122b provided thereto. The second end is provided with coupling flange 124a, 124b which couples with water-tight chamber 150a, 150b which contains brass waveguide 140a, 140b and magnetron 160a, 160b. The magnetron 160a, 160b acts as a microwave energy source to feed microwaves into the brass waveguide 140a, 140b and thence to the ultraviolet lamp 110a, 110b which is excited thereby.

The enclosure 120a, 120b is within tubular housing 170a, 170b. The housing 170a, 170b has a fluid inlet 172a, 172b and a fluid outlet 174a, 174b provided thereto. In use, fluid flows from the inlet 172a, 172b past the enclosure 120a, 120b and towards the outlet 174a, 174b. As the fluid flows past the enclosure 120a, 120b it is irradiated with UV radiation produced by the ultraviolet lamp 110a, 110b. The radiation itself passes through the UV transparent walls of the enclosure 120a, 120b to contact the fluid.

FIGS. 3a and 3b show ultraviolet light sources similar in structure to the ultraviolet light sources of FIGS. 2a and 2b but for use in treatment of airborne substances. Both comprise ultraviolet mercury discharge lamp 210a, 210b enclosed by cylindrical enclosure 220a, 220b. The cylindrical walls of the enclosure 220a, 220b form a waveguide and are comprised of quartz material which is transparent to UV radiation. A conducting copper mesh 230a, 230b is provided to the inner surface of the waveguide. The enclosure 220a, 220b has air or nitrogen circulating therein. First end of the cylindrical enclosure has blocking end flange 222a, 222b provided thereto. The second end is provided with coupling flange 224a, 224b which couples with airtight chamber 250a, 250b containing brass waveguide 240a, 240b and magnetron 260a, 260b. The magnetron 260a, 260b acts as a microwave energy source to feed microwaves into brass waveguide 240a, 240b and thence to the ultraviolet lamp 210a, 210b which is excited thereby.

The enclosure 220a, 220b is within tubular housing 270a, 270b. The housing 270a, 270b has an air inlet 272a, 272b and an air outlet 274a, 274b provided thereto. In use, air flows from the inlet 272a, 272b past the enclosure 220a, 220b and towards the outlet 274a, 274b. As the air flows past the enclosure 220a, 220b it is irradiated with UV radiation produced by the ultraviolet lamp 210a, 210b. The radiation itself passes through the UV transparent walls of the enclosure 220a, 220b to contact the air, thereby treating the molecular entities carried in the air.

FIG. 4 shows a cabinet ultraviolet light source herein suitable for use in treating objects herein. Ultraviolet mercury discharge lamp 310 is enclosed by cylindrical enclosure 320. The cylindrical walls of the enclosure 320 form a waveguide and are comprised of quartz material which is transparent to UV radiation but only partially transparent to microwave radiation. A conducting copper mesh 330 is provided to the inner surface of the waveguide. The enclosure 320 optionally has air or nitrogen circulating therein. First end of the cylindrical enclosure has blocking end flange 322 provided thereto. The second end is provided with coupling flange 324 which couples with linear pathguide 340 which in turn connects with magnetron 360. The magnetron 360 acts as a microwave energy source to feed microwaves into pathguide 340 and thence to the ultraviolet lamp 310 which is excited thereby.

The enclosure 320 is within housing 370 which has an entry door 380 provided thereto. In use, items to be treated are placed in the housing 370. The items are irradiated with UV radiation produced by the ultraviolet lamp 310 and by microwave radiation deriving from the magnetron 360. The radiation itself passes through the UV transparent and microwave partially transparent walls of the enclosure 320 to contact the items. Optionally, the housing 370 may be provided with UV transparent shelves for the items. An inner reflective lining, for example an aluminium foil lining, may also be provided to the housing 370.

Figure 5:
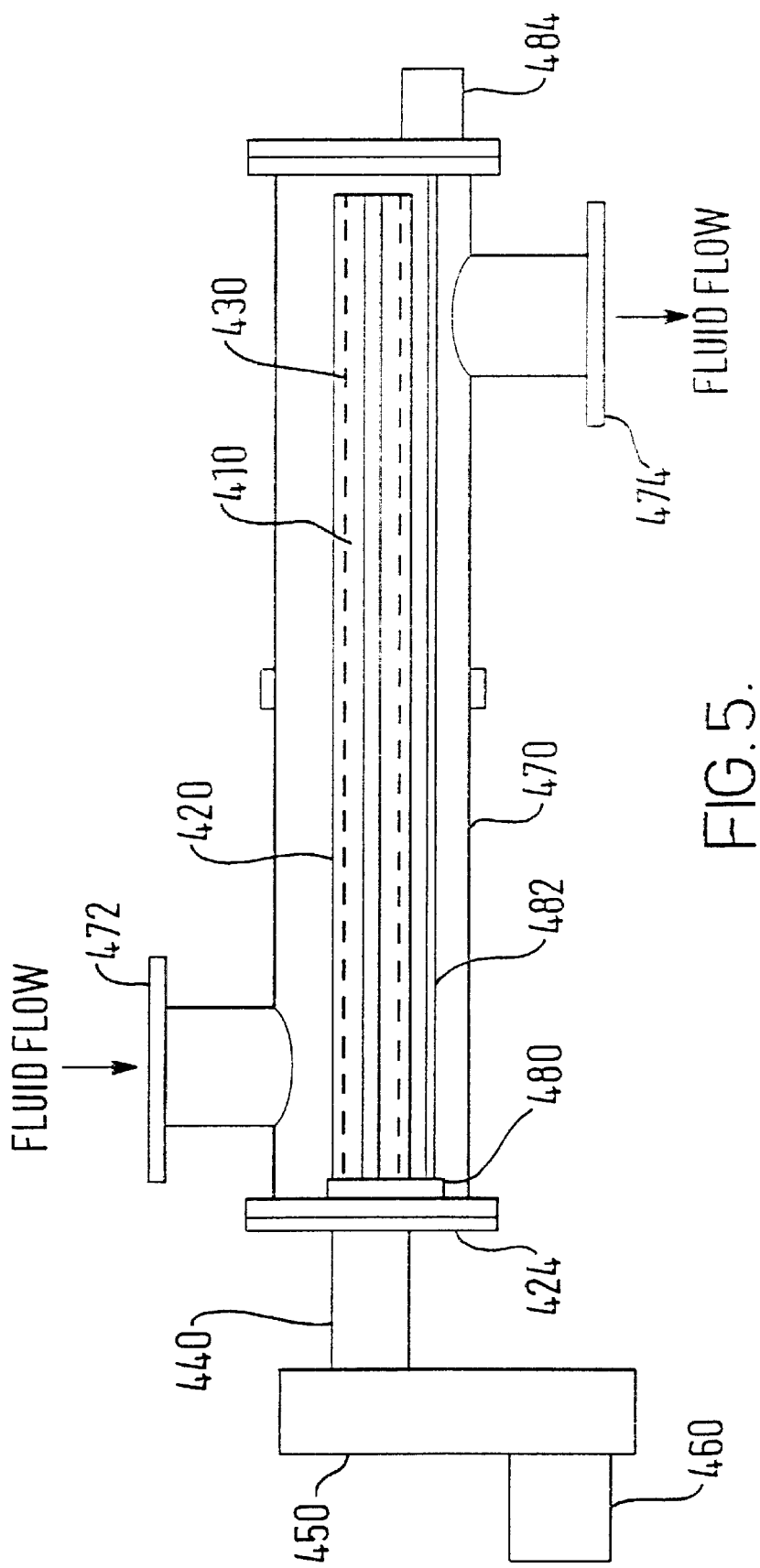
FIG. 5 is a schematic representation of a seventh ultraviolet light source herein.

FIG. 5 shows an ultraviolet light source comprising an ultraviolet bulb 410 enclosed by cylindrical enclosure 420. The cylindrical walls of the enclosure 420 form a waveguide and are comprised of quartz material which is transparent to UV radiation. The quartz tube enclosure 420 is provided with a cleaning system comprising wiper 480 which is mounted for movement on track 482. The track 482 is arranged parallel to the enclosure 420 and the movement of the wiper 480 is powered by motor 484.

A conducting copper mesh 430 is provided to the inner surface of the waveguide. An end of the enclosure 420 couples with coupling flange 424 which couples with stainless steel cylindrical pathguide 440 which in turn connects with stainless steel rectangular pathguide 450. Magnetron 460 acts as a microwave energy source to feed microwaves into the rectangular pathguide 450, thence into the cylindrical pathguide 440 and finally to the ultraviolet lamp 410 which is excited thereby.

The enclosure 420 is within stainless steel housing 470. The housing 470 has a fluid inlet 472 and a fluid outlet 474 provided thereto. In use, fluid flows from the inlet 472 past the enclosure 420 and towards the outlet 474. As the fluid flows past the enclosure 420 it is irradiated with UV radiation produced by the ultraviolet bulb 410. The radiation itself passes through the UV transparent walls of the enclosure 420 to contact the fluid.

Figure 6:
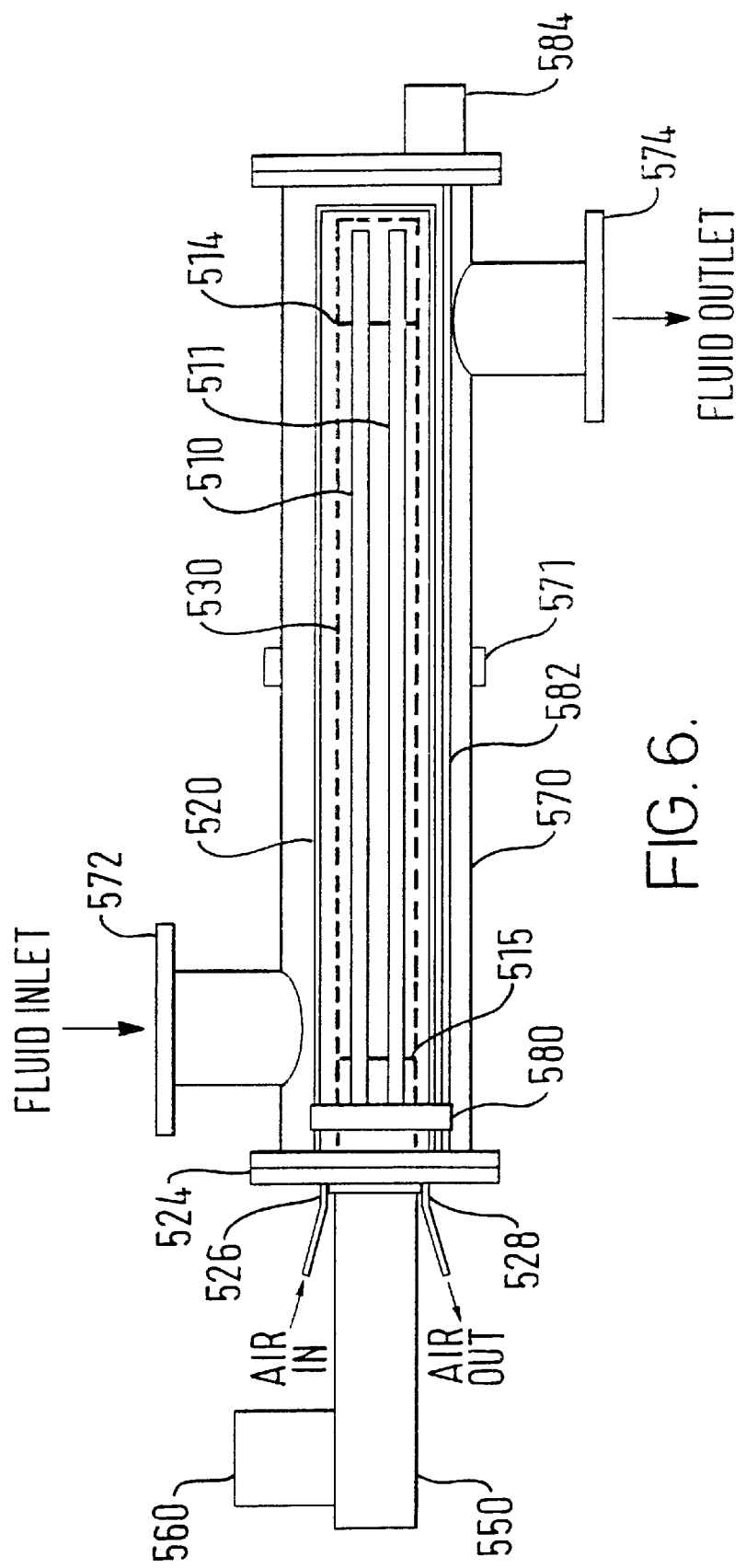
FIG. 6 is a schematic representation of an eighth ultraviolet light source herein.

FIG. 6 shows an ultraviolet light source comprising two ultraviolet bulbs 510, 511 fixed in a mutually parallel arrangement by lamp supports 514, 515. The bulbs 510, 511 are enclosed by cylindrical enclosure 520. An air coolant system is provided to the bulb 510 wherein cooling air is fed into the enclosure 520 through air inlet 526 and circulates past the bulb before exiting at air outlet 528. The cylindrical walls of the enclosure 520 form a waveguide and are comprised of quartz material which is transparent to UV radiation. The quartz tube enclosure 520 is provided with a cleaning system comprising wiper 580 which is mounted for movement on track 582. The track 582 is arranged parallel to the enclosure 520 and the movement of the wiper 580 is powered by motor 584.

A conducting copper mesh 530 is provided to the inner surface of the waveguide. An end of the enclosure 520 couples with coupling flange 524 which couples with stainless steel rectangular pathguide 550. Magnetron 560 acts as a microwave energy source to feed microwaves into the rectangular pathguide 550 and thence to the ultraviolet lamp 510 which is excited thereby.

The enclosure 520 is within stainless steel housing 570 having observation port 571. The housing 570 has a fluid inlet 572 and a fluid outlet 574 provided thereto. In use, fluid flows from the inlet 572 past the enclosure 520 and towards the outlet 574. As the fluid flows past the enclosure 520 it is irradiated with UV radiation produced by the ultraviolet bulbs 510, 511. The radiation itself passes through the UV transparent walls of the enclosure 520 to contact the fluid.

Figure 7:
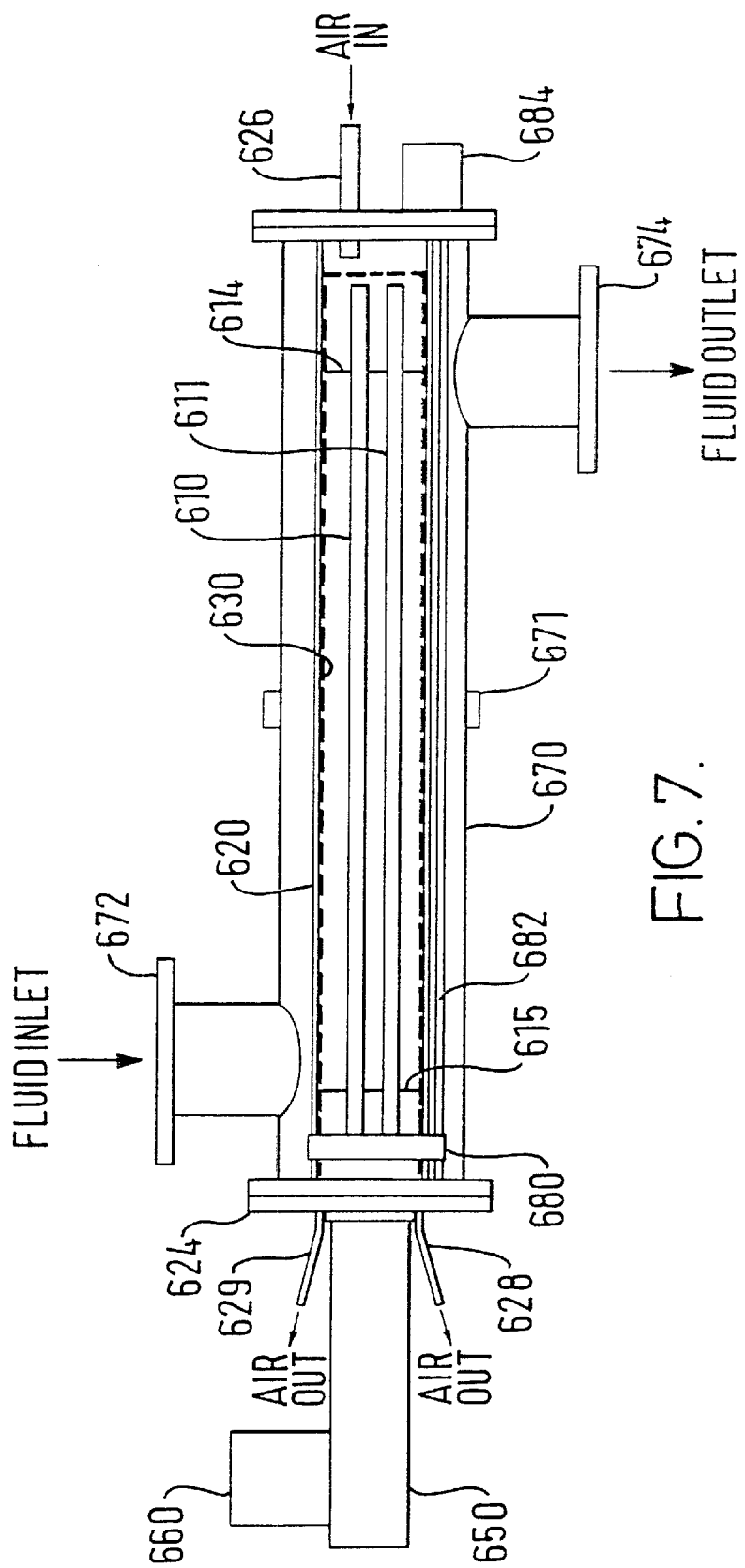
FIG. 7 is a schematic representation of a ninth ultraviolet light source herein.

FIG. 7 shows an ultraviolet light source comprising two ultraviolet bulbs 610, 611 fixed in a mutually parallel arrangement by lamp supports 614, 615. The bulbs 610, 611 are enclosed by cylindrical enclosure 620. An air coolant system is provided to the bulbs 610, 611 wherein cooling air is fed into the enclosure 620 through air inlet 626 and flows past the bulbs 610, 611 before exiting at air outlets 628, 629. The cylindrical walls of the enclosure 620 form a waveguide and are comprised of quartz material which is transparent to UV radiation. The quartz tube enclosure 620 is provided with a cleaning system comprising wiper 680 which is mounted for movement on track 682. The track 682 is arranged parallel to the enclosure 620 and the movement of the wiper 680 is powered by motor 684.

A conducting copper mesh 630 is provided to the inner surface of the waveguide. An end of the enclosure 620 couples with coupling flange 624 which couples with stainless steel rectangular pathguide 650. Magnetron 660 acts as a microwave energy source to feed microwaves into the rectangular pathguide 650 and thence to the ultraviolet bulbs 610, 611 which are excited thereby.

The enclosure 620 is within stainless steel housing 670 having observation port 671. The housing 670 has a fluid inlet 672 and a fluid outlet 674 provided thereto. In use, fluid flows from the inlet 672 past the enclosure 620 and towards the outlet 674. As the fluid flows past the enclosure 620 it is irradiated with UV radiation produced by the ultraviolet bulbs 610, 611. The radiation itself passes through the UV transparent walls of the enclosure 620 to contact the fluid.

Figure 8:
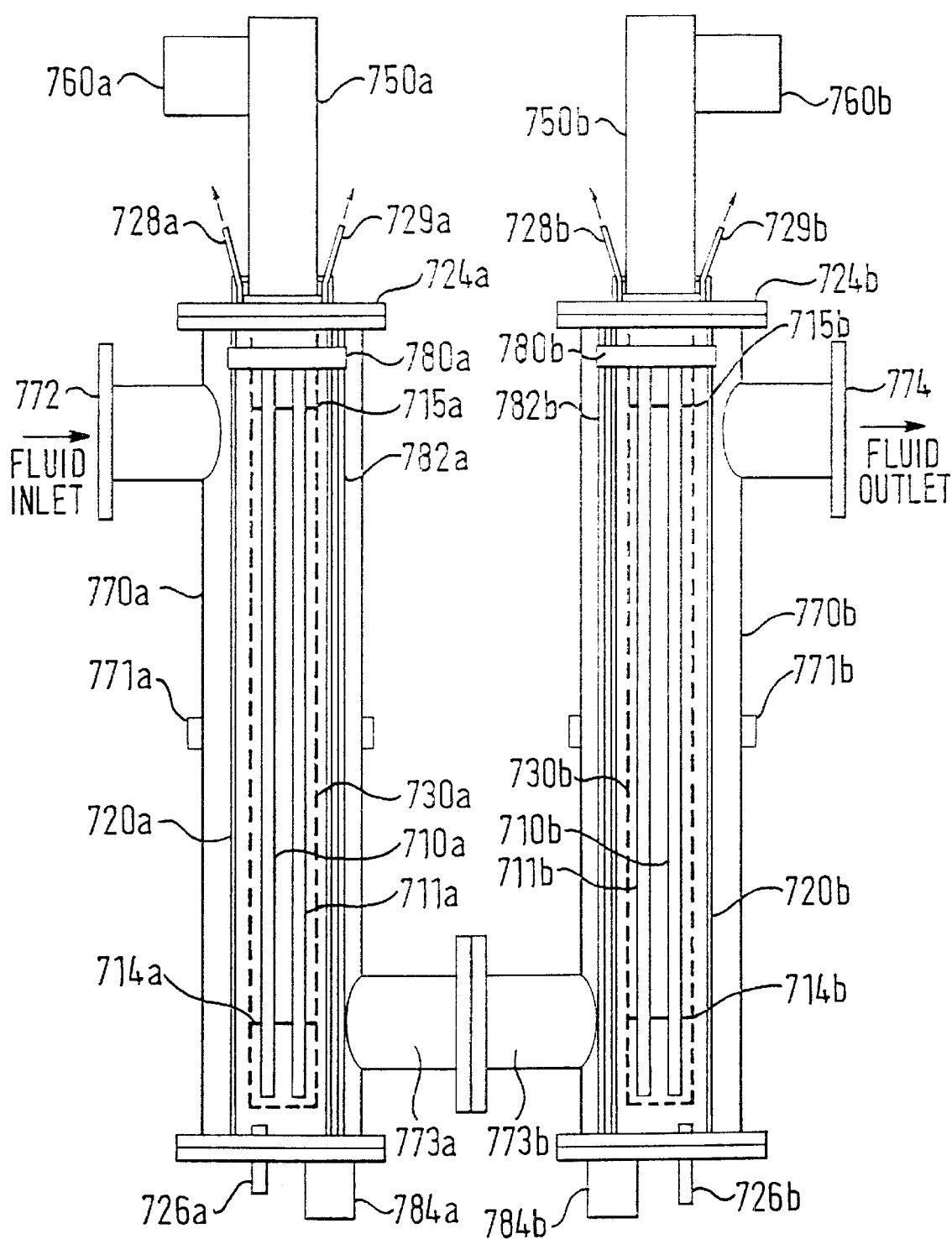
FIG. 8 is a schematic representation of a tenth ultraviolet light source herein.

FIG. 8 shows an ultraviolet light source based on a series arrangement of a pair of ultraviolet light sources of the type illustrated in FIG. 7. The ultraviolet source comprises two pairs of ultraviolet bulbs 710a, 711a and 710b, 711b fixed in a mutually parallel arrangement by lamp supports 714a, 715a and 714b, 715b. The bulbs 710a, 711a and 710b, 710b are each enclosed by cylindrical enclosures 720a, 720b. An air coolant system is provided each pair of bulbs 710a, 711a and 710b, 711b wherein cooling air is fed into the enclosures 720a, 720b through air inlets 726a, 726b and flows past the bulbs 710a, 711a and 710b, 711b before exiting at air outlets 728a, 729a and 728b, 729b. The cylindrical walls of the enclosures 720a, 720b form a waveguide and are comprised of quartz material which is transparent to UV radiation. The quartz tube enclosures 720a, 720b are each provided with a cleaning system comprising wiper 780a, 780b which is mounted for movement on respective track 782a, 782b. The tracks 782a, 782b are arranged parallel to the enclosures 720a, 720b and the movement of the wipers 780a, 780b is powered by motors 784a, 784b.

A conducting copper mesh 730a, 730b is provided to the inner surface of the waveguide. An end of each enclosure 720a, 720b couples with coupling flange 724a, 724b which couples with stainless steel rectangular pathguide 750a, 750b. Magnetrons 760a, 760b act as microwave energy sources to feed microwaves into the respective rectangular pathguides 750a, 750b and thence to the ultraviolet bulbs 710a, 711a and 710b, 711b which are excited thereby.

The enclosures 720a, 720b are within a stainless steel housing comprising two interconnected arms 770a, 770b each having an observation port 771a, 771b. The first arm of the housing 770a has a fluid inlet 772 and the second arm of the housing 770b has a fluid outlet 774 provided thereto. In use, fluid flows from the inlet 772 past the first enclosure 720a, through passages 773a, 773b, then past the second enclosure 720b and finally towards the outlet 774. As the fluid flows past the enclosures 720a, 720b it is irradiated with UV radiation produced by the ultraviolet bulbs 710a, 711a and 710b, 711b. The radiation itself passes through the UV transparent walls of the enclosures 720a, 720b to contact the fluid.

Whilst in each of FIGS. 1 to 8 the magnetron is arranged locally to the lamp it may be appreciated that in other embodiments the magnetron is distally located and communicates with the lamp via a coaxial cable feed arrangement. Such coaxial cable feed arrangements are known in the art for example, described in Japanese Patent Publication No. 61046290.

Figure 9:
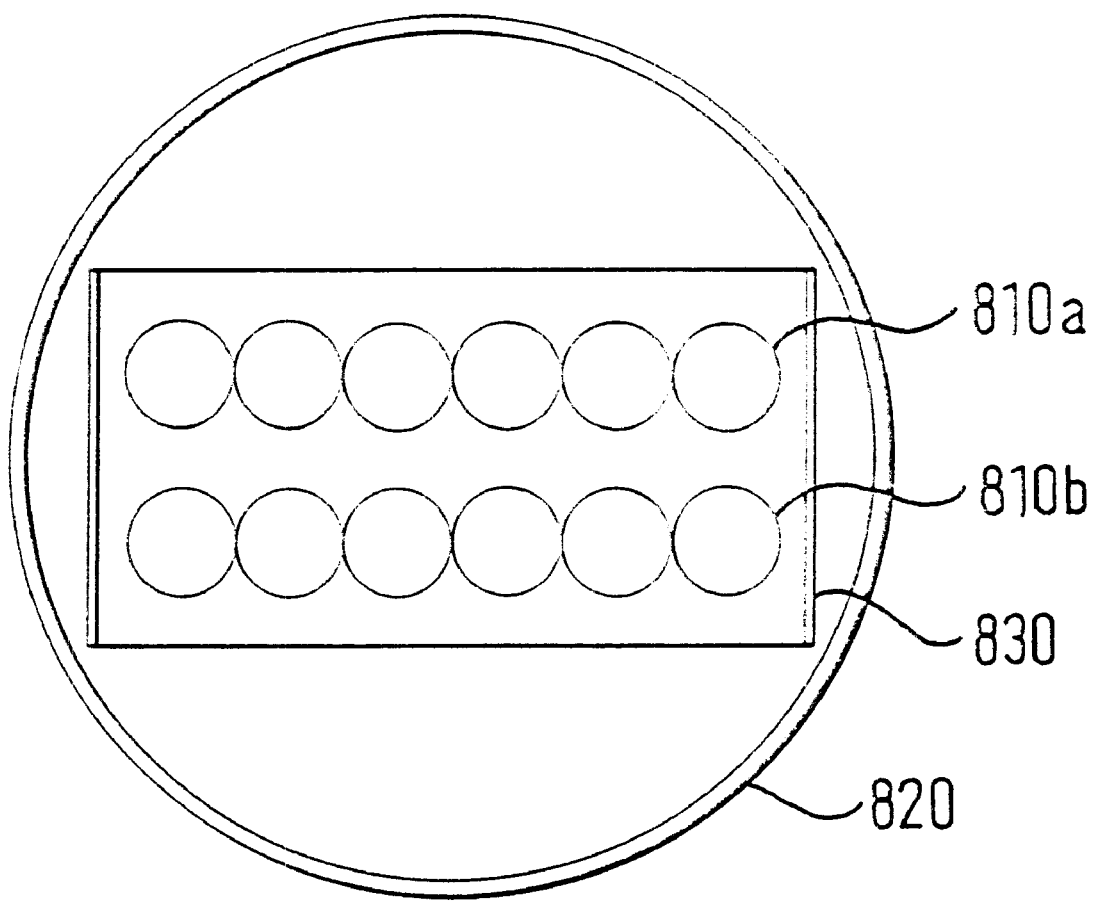
FIG. 9 is a cross-sectional view of an ultraviolet lamp herein.

FIG. 9 shows in cross-sectional view an ultraviolet lamp herein. The lamp comprises two rows 810a, 810b of six bulbs forming a six by two lamp array arrangement. The array of bulbs 810a, 810b is surrounded by a copper mesh 830 having a rectangular cross-section. Both the array of bulbs 810a, 810b and the copper mesh 830 are enclosed by a quartz tube 820 having a circular cross-section.

It may be appreciated that lamps comprising plural bulbs in any suitable arrangement may be employed in variations of the ultraviolet light sources shown in FIGS. 1 to 8.

What is claimed is:

1. An ultraviolet light source comprising
   an ultraviolet bulb;
   a microwave energy source for exciting said ultraviolet bulb; and
   an optically transparent waveguide for guiding microwave energy originating from said microwave energy source to the ultraviolet bulb, wherein said waveguide wholly surrounds the ultraviolet bulb, and wherein the dominant wavelength of the ultraviolet light source is either
(a) from 140 to 240 nm and the ultraviolet light source is suitable for use in promoting molecular dissociation reactions; or
(b) from 300 to 400 nm and the ultraviolet light source is suitable for use in promoting photochemical reactions.

2. An ultraviolet light source according to claim 1, wherein the dominant wavelength of the ultraviolet light source is from 160 to 200 nm.

3. An ultraviolet light source according to claim 1, wherein the dominant wavelength of the ultraviolet light source is from 330 to 370 nm.

4. An ultraviolet light source according to claim 1, wherein the ultraviolet bulb has no electrode.

5. An ultraviolet light source according to claim 1, wherein the waveguide controls the flow of microwave energy therefrom.

6. An ultraviolet light source according to claim 5, wherein the waveguide blocks a majority of the flow of microwave energy therefrom.

7. An ultraviolet light source according to claim 1, wherein the waveguide comprises quartz or a UV-transparent plastic material.

8. An ultraviolet light source according to claim 1, wherein the waveguide comprises a conducting material.

9. An ultraviolet light source according to claim 8, wherein the conducting material is a coating or liner to the waveguide.

10. An ultraviolet light source according to claim 8, wherein the waveguide comprises a conducting mesh.

11. An ultraviolet light source according to claim 10, wherein the conducting mesh comprises a material selected from the group consisting of copper, aluminium and stainless steel.

12. An ultraviolet light source according to claim 1, wherein the ultraviolet bulb has an elongate form.

13. An ultraviolet light source according to claim 1, comprising plural ultraviolet bulbs.

14. An ultraviolet light source according to claim 13, comprising from 2 to 25, preferably from 3 to 18 bulbs.

15. An ultraviolet light source to claim 13, wherein said plural ultraviolet bulbs form an arrangement selected from the group consisting of a random arrangement, a side-by-side arrangement, a sequential arrangement, an array arrangement and a cluster arrangement.

16. An ultraviolet light source according to claim 1, wherein the optically transparent waveguide has a cylindrical or rectangular form.

17. An ultraviolet light source according to claim 1, wherein the microwave energy source comprises a magnetron.

18. An ultraviolet light source according to claim 1, additionally comprising a system for cleaning the enclosure.

19. An ultraviolet light source according to claim 1, additionally comprising a pathguide to guide the microwave energy from the microwave energy source to the ultraviolet bulb.

20. An ultraviolet light source according to claim 19, wherein the pathguide defines an essentially linear path.

21. An ultraviolet light source according to claim 19, wherein the pathguide defines a non-linear path.

22. An ultraviolet light source according to claim 19, wherein the pathguide comprises a coaxial cable.

23. An ultraviolet light source according to claim 1, additionally comprising a housing for said waveguide.

24. An ultraviolet light source according to claim 23, wherein the housing has an inlet and an outlet and the housing is shaped to guide fluid flow from the inlet, past the waveguide to the outlet.

25. An ultraviolet light source according to claim 24, wherein said fluid comprises water or air.

26. An ultraviolet light source according to claim 24, additionally comprising a pump for pumping fluid from the inlet, past the enclosure to the outlet.

27. A lamp comprising
an ultraviolet bulb, said bulb being excitable by microwave energy; and
an optically transparent waveguide for guiding microwave energy originating from a microwave energy source to the ultraviolet bulb, wherein said waveguide wholly surrounds the ultraviolet bulb, and
wherein the dominant wavelength of the lamp is either
(a) from 140 to 240 nm and the lamp is suitable for use in promoting molecular dissociation reactions; or
(b) from 300 to 400 nm and the lamp is suitable for use in promoting photochemical reactions.

28. A lamp according to claim 27, wherein the dominant wavelength of the lamp is from 160 to 200 nm.

29. A lamp according to claim 28, wherein the dominant wavelength of the lamp is from 330 to 370 nm.

30. A lamp according to claim 27, wherein the ultraviolet bulb has no electrode.

31. A method of promoting the dissociation of a molecular entity comprising
applying microwave energy to an ultraviolet lamp to produce ultraviolet radiation of dominant wavelength of from 140 to 240 nm; and
exposing the molecular entity to said ultraviolet radiation, wherein
an optically transparent waveguide guides said microwave energy to said ultraviolet lamp and said waveguide wholly surrounds the ultraviolet lamp.

32. A method according to claim 31, wherein the molecular entity is borne in a fluid such as air or a liquid and the substance-bearing fluid flows past the enclosure.

33. A method according to claim 31, wherein the molecular entity is an organic material.

34. A method according to claim 33, wherein the organic material is oxidisable.

35. A method according to claim 34, for the dissociation of Total Oxidisable Carbon (TOC) in water.

36. A method according to claim 31, wherein the molecular entity is borne on a surface and the ultraviolet radiation is applied to said surface.

37. A method according to claim 36, wherein the molecular entity is a contaminant on the surface.

38. A method according to claim 36, wherein the surface is of a product selected from the group consisting of food products, packaging products and the surfaces of any equipment employed in the manufacture thereof.

39. A method of promoting a photochemical reaction in a substance comprising
applying microwave energy to an ultraviolet lamp to produce ultraviolet radiation having a dominant wavelength of from 300 to 400 nm; and
exposing an entity to said ultraviolet radiation,
wherein an optically transparent waveguide guides said microwave energy to said ultraviolet lamp and said waveguide wholly surrounds the lamp.

40. A method according to claim 39, wherein the substance is borne in a fluid such as air or a liquid and the substance-bearing fluid flows past the enclosure.

41. A method according to claim 39, wherein the substance is borne on a surface and the ultraviolet radiation is applied to the surface.

42. An ultraviolet light source comprising a plurality of ultraviolet bulbs;

a microwave energy source for exciting said plurality of ultraviolet bulbs; and an optically transparent waveguide for guiding microwave energy originating from said microwave energy source to the plurality of ultraviolet bulbs, wherein said waveguide wholly surrounds the plurality of ultraviolet bulbs.

43. A lamp comprising a plurality of ultraviolet bulbs, said plurality of bulbs being excitable by microwave energy; and an optically transparent waveguide for guiding microwave energy originating from a microwave energy source to the plurality of ultraviolet bulbs, wherein said waveguide wholly surrounds the plurality of ultraviolet bulbs.

* * * * *